United States Patent [19]

Hickle et al.

[11] Patent Number: 5,098,705

[45] Date of Patent: * Mar. 24, 1992

[54] USE OF A BACILLUS THURINGIENSIS MICROBE FOR CONTROLLING LESSER MEALWORM, ALPHITOBIUS DIAPERINUS

[75] Inventors: Leslie A. Hickle; Gregory A. Bradfisch; Jewel M. Payne, all of San Diego, Calif.

[73] Assignee: Mycogen Corporation, San Diego, Calif.

[*] Notice: The portion of the term of this patent subsequent to Mar. 12, 2008 has been disclaimed.

[21] Appl. No.: 580,704

[22] Filed: Sep. 11, 1990

Related U.S. Application Data

[63] Continuation-in-part of Ser. No. 155,189, Feb. 12, 1988, Pat. No. 4,999,192.

[51] Int. Cl.$^5$ .................. C12N 1/20; C12N 1/22; A01N 63/00; A01N 65/00
[52] U.S. Cl. .................. 424/93 L; 424/DIG. 8; 424/195.1; 424/93 A; 435/252.5; 435/832; 435/252.31; 435/172.3; 514/2; 530/370; 530/350; 800/200; 935/63; 935/64
[58] Field of Search .............. 424/93, 195.1; 405/252.1, 252.5, 832, 252.31, 172.3; 500/350, 825, 370; 800/200; 935/63, 64

[56] References Cited

U.S. PATENT DOCUMENTS

| | | | |
|---|---|---|---|
| 4,849,217 | 7/1989 | Soares et al. | 424/93 |
| 4,910,016 | 3/1990 | Gaertner et al. | 424/93 |
| 4,948,734 | 8/1990 | Edwards et al. | 424/93 X |
| 4,950,471 | 8/1990 | Travers et al. | 424/93 |
| 4,999,192 | 3/1991 | Payne et al. | 424/93 |

OTHER PUBLICATIONS

Beegle, C. C. (1978) "Use of Entomogenous Bacteria in Agroecosystems," Developments in Industrial Microbiology 20: 97–104.

Couch, T. L. (1980) "Mosquito Pathogenicity of *Bacillus thuringiensis* var. *israelensis*, "Developments in Industrial Microbiology 22: 61–67.

*Primary Examiner*—Howard E. Schain
*Attorney, Agent, or Firm*—Saliwanchik & Saliwanchik

[57] ABSTRACT

The subject invention concerns the use of a novel and useful bioinsecticide against the lesser mealworm (*Alphitobius diaperinus*). The lesser mealworm is a devastating pest in the poultry industry. The bioinsecticide of the subject invention is a novel *B. thuringiensis* microbe referred to as B.t. PS40D1, or mutants thereof. The spores or toxin crystals of this microbe are useful to control the lesser mealworm in various environments.

6 Claims, No Drawings

USE OF A BACILLUS THURINGIENSIS MICROBE FOR CONTROLLING LESSER MEALWORM, ALPHITOBIUS DIAPERINUS

CROSS-REFERENCE TO A RELATED APPLICATION

This is a continuation-in-part of co-pending application Ser. No. 07/155,189, filed Feb. 12, 1988, now U.S. Pat. No. 4,999,192.

BACKGROUND OF THE INVENTION

*Bacillus thuringiensis* (B.t.) produces an insect toxin designated as δ-endotoxin. It is synthesized by the B.t. sporulating cell. The toxin, upon being ingested in its crystalline form by susceptible insect larvae, is transformed into biologically active moieties by the insect gut juice proteases. The primary target is insect cells of the gut epithelium, which are rapidly destroyed.

The reported activity spectrum of B.t. covers insect species within the order Lepidoptera, many of which are major pests in agriculture and foresty. The activity spectrum also includes the insect order Diptera, which includes mosquitos and black flies. See Couch, T. L. (1980) "Mosquito Pathogenicity of *Bacillus thuringiensis* var. israelensis," Developments in Industrial Microbiology 22:61-76; Beegle, C. C., (1978) "Use of Entomogenous Bacteria in Agroecosystems," Developments in Industrial Microbiology 20:97-104. U.S. Pat. No. 4,910,016 discloses a B.t. strain active against coleopteran and lepidopteran pests. U.S. Pat. No. 4,849,217 discloses a B.t. strain which is active against the Egyptian alfalfa weevil.

The lesser mealworm (*Alphitobius diaperinus*) is a cosmopolitan pest of households, stored grain facilities, and poultry houses. It usually feeds on damp and moldy grain, milled products, and spoiled foods. Due to significant growth in the poultry industry in recent years, this insect has become one of the major pest species present in the litter and structural components of poultry houses. The larvae of *A. diaperinus* ingest chicken feed and other organic matter (including dead or moribund chicks), are reservoirs for a multitude of pathogens which are threats to poultry production, and cause extensive structural damage to poultry houses by tunneling into the insulation and soft wood of the facility. The loss of insulation due to the holes and tunnels bored by *A. diaperinus* larvae results in greater heating costs as well as poorer feed conversion efficiency by poultry due to the lack of adequate temperature control in the poultry houses. Additionally, since poultry will feed on these insects as an alternative food source, they may experience lesser weight gains than if fed their normal nutrient balanced diet. The larvae of *A. diaperinus* have also been implicated in causing lesions on poultry and may increase their susceptibility to disease due to dust stirred up by the birds while they are scratching for insects. *A. diaperinus* may also cause allergic reactions in humans.

Current control techniques are inadequate for controlling this pest and will not eradicate the pest problem. They include the following: 1) thoroughly cleaning the poultry house and having it remain empty for a prolonged period of time; 2) applying insecticides to the structure and floors of the house after it is cleaned; 3) using insect growth regulators; and 4) using steinernematid and heterorhabditid nematodes as beetle entomopathogens. These methods are ineffective and expensive. Thus, there is an urgent need for the effective control of the lesser mealworm.

BRIEF SUMMARY OF THE INVENTION

The subject invention concerns the use of a novel *Bacillus thuringiensis* (B.t.) isolate. This novel B.t. isolate, known herein as *Bacillus thuringiensis* PS40D1 (B.t. PS40D1), has been shown, unexpectedly and advantageously, to be active against the pest known as the lesser mealworm (*Alphitobius diaperinus*).

The subject invention also includes the use of mutants of B.t. PS40D1 which have substantially the same pesticidal properties as B.t. PS40D1. Procedures for making mutants are well known in the microbiological art. Ultraviolet light and nitrosoguanidine are used extensively toward this end.

Further, the invention also includes the use of treated cells of substantially intact B.t. PS40D1 cells, or mutants thereof, to prolong the pesticidal activity when the substantially intact cells are applied to the environment of the lesser mealworm. Such treatment can be by chemical or physical means, or a combination of chemical or physical means, so long as the technique does not deleteriously affect the properties of the pesticide, nor diminish the cellular capability in protecting the pesticide. The treated B.t. PS40D1 cell acts as a protective coating for the pesticidal toxin. The toxin becomes available to act as such upon ingestion by the lesser mealworm.

DETAILED DISCLOSURE OF THE INVENTION

The novel *Bacillus thuringiensis* isolate of the subject invention is characterized in U.S. application Ser. No. 07/155,189, filed on Feb. 12, 1988, now U.S. Pat. No. 4,999,192. That characterization is incorporated herein by reference to said application.

The culture disclosed in this application has been deposited in the Agricultural Research Service Patent Culture Collection (NRRL), Northern Regional Research Center, 1815 North University Street, Peoria, Ill. 61604, U.S.A.

| Culture | Repository No. | Deposit date |
|---|---|---|
| *Bacillus thuringiensis* PS40D1 | NRRL B-18300 | Feb. 3, 1988 |

The subject culture has been deposited under conditions that assure that access to the culture will be available during the pendency of this patent application to one determined by the Commissioner of Patents and Trademarks to be entitled thereto under 37 CFR 1.14 and 35 U.S.C. 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the data of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

B.t. PS40D1, NRRL B-18300, can be cultured using standard art media and fermentation techniques. Upon completion of the fermentation cycle, the bacteria can be harvested by first separating the B.t. spores and toxin crystals from the fermentation broth by means well known in the art. The recovered B.t. spores and/or toxin crystals can be formulated into a wettable powder, spray, liquid concentrate, granules, or other formulations by the addition of surfactants, dispersants, inert carriers and other components to facilitate handling and application for particular target pests. These formulation and application procedures are all well known in the art. Since the B.t. spores and/or toxin crystals of the invention are non-toxic to humans or animals, the use of excess amounts of such is not detrimental. It is well within the skill of those in this art to use levels of the B.t. spores and/or toxin crystals which provide optimum pesticidal results with minimum costs.

Formulated products can be sprayed or applied onto areas inhabited by the lesser mealworm.

Another approach that can be taken is to incorporated the spores and toxin crystals of B.t. PS40D1 into bait granules containing an attractant and applying these granules to the soil for control of the lesser mealworm.

The B.t. PS40D1 cells can be treated prior to formulation to prolong the pesticidal activity when the cells are applied to the environment of the lesser mealworm. Such treatment can be by chemical or physical means, or by a combination of chemical and/or physical means, so long as the technique does not deleteriously affect the properties of the pesticide, nor diminish the cellular capability in protecting the pesticide. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride; alcohols, such as isopropyl and ethanol; various histologic fixatives, such as Bouin's fixative and Helly's fixative (See: Humason, Gretchen L., Animal Tissue Techniques, W. H. Freeman and Company, 1967); or a combination of physical (heat) and chemical agents that prolong the activity of the toxin produced in the cell when the cell is applied to the environment of the target pest(s). Examples of physical means are short wavelength radiation such as gamma-radiation and X-radiation, freezing, UV irradiation, lyophilization, and the like.

The gene(s) from the novel B.t. isolate of the subject invention can be introduced into other microbes. The toxin(s) expressed by the gene(s) can be used to control the lesser mealworm. Such toxins can be formulated by standard techniques into suitable sprays and, also, incorporated into poultry feed.

A wide variety of ways are known and available for introducing the B.t. gene(s) expressing the toxin into the microorganism host under conditions which allow for stable maintenance and expression of the gene. The transformants can be isolated in accordance with conventional ways, usually employing a selection technique, which allows for selection of the desired organism as against unmodified organism or transferring organisms, when present. The transformants then can be tested for lesser mealworm activity.

Suitable host cells, where the cells will be treated to prolong the activity of the toxin in the cell when the then treated cell is applied to the environment of the lesser mealworm, may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the B.t. gene into the host, availability of expression systems, efficiency of expression, stability of the toxin in the host, and the presence of auxiliary genetic capabilities. Characteristics of interest for use as a microcapsule include protective qualities for the toxin, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis*, and the like.

The transformed host microbe containing the B.t. gene(s) of the subject invention can be used, if desired, without treatment, as described above, to control the lesser mealworm.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing B.t. PS40D1, NRRL B-18300

A subculture of B.t. PS40D1, NRRL B-18300 can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and/or toxin crystals, obtained in the above fermentation, can be isolated by procedures well known in the art. A frequently-used procedure is to subject the harvested fermentation broth to separation techniques, e.g., centrifugation.

EXAMPLE 2

Testing of B.t. PS40D1, NRRL B-18300 Spores and Toxin Crystals Against the Lesser Mealworm B.t. PS40D1, NRRL B-18300 spores and toxin crystals were tested against the lesser mealworm. The assay was conducted as follows:

Lesser mealworm first or second instar larvae were exposed to a preparation of B.t. PS40D1 on a feeding substrate consisting of a poultry feed slurry. The assay was incubated for 6 days and the mortality assessed by noting dead/alive larvae. Each test was replicated several times.

B.t. PS40D1 was found to be active in the above test. The percent mortality was 60.

In view of the above test result, B.t. PS40D1 (isolate and/or toxin) can be used to control the lesser mealworm populations through several mechanisms: 1) as a feed through in poultry where the residual in the poultry feces would be toxic to the mealworm (the material could be placed in the chicke feed, water, mineral/vitamin supplement, on in combination with other therapeutic agents); 2) as a surface spray which could be used to treat structural components, insulation, litter, floors, cages, or other areas where beetles reside and feed; and 3) as a bait spray or formulation where the beetles would be attracted to the food substrate or attractant, eat the B.t. PS40D1 treated bait and die or become moribund or less fit, thus reducing the populations of the beetles.

The use of this biocontrol agent is advantageous because it is environmentally benign, and B.t. microbes, as a class, are well known effective biological control agents for other pest species. They provide long term population control of insects without consideration for toxic or residual toxicity effects attributed to the current synthetic chemicals which are utilized.

Since there is no known way to predict which insects the subject B.t. isolate may be active against, it is necessary to conduct tests against each insect species in order to determine whether there is activity against such insect. For example, tests are presently being conducted against dermestid beetles, for example, *Dermestes maculatus* and *Dermestes lardarius*, which are also found in poultry houses. Thus, work is continuing on the subject B.t. isolate to determine whether it or its toxins can be used to control other insects.

We claim:

1. A process for controlling the lesser mealworm which comprises contacting said pest, or the environment of said pest, with an effective amount of *Bacillus thuringiensis* PS40D1 spores or toxin crystals, having the identifying characteristics of NRRL B-18300, or mutants thereof.

2. A process, according to claim 1, wherein said insect pest is contacted with an insect-controlling sufficient amount of *Bacillus thuringiensis* PS40D1 spores or toxin crystals, or mutants thereof, by incorporating said *Bacillus thuringiensis* PS40D1 into a poultry feed.

3. A process, according to claim 1, wherein said insect pest is contacted with an insect-controlling sufficient amount of *Bacillus thuringiensis* PS40D1 spores or toxin crystals, or mutants thereof, by incorporating said *Bacillus thuringiensis* PS40D1 into a surface spray.

4. A process, according to claim 1, wherein said insect pest is contacted with an insect-controlling sufficient amount of *Bacillus thuringiensis* PS40D1 spores or toxin crystals, or mutants thereof, by incorporating said *Bacillus thuringiensis* PS40D1 into a bait spray or formulation.

5. A process, according to claim 1, wherein substantially intact *Bacillus thuringiensis* PS40D1 cells, or mutants thereof, are treated to prolong the pesticidal activity when the substantially intact cells are applied to the environment of the lesser mealworm.

6. A process for controlling the lesser mealworm which comprises contacting said pest, or the environment of said pest, with an effective amount of a toxin(s) obtained from *Bacillus thuringiensis* PS40D1, having the identifying characteristics of NRRL B-18300, or mutants thereof.

* * * * *